United States Patent

Santi et al.

[11] Patent Number: 5,936,051
[45] Date of Patent: Aug. 10, 1999

[54] SUBSTITUTED METALLOCENE CATALYST FOR THE (CO)POLYMERIZATION OF OLEFINS

[75] Inventors: Roberto Santi; Giampiero Borsotti, both of Novara; Cecilia Querci, Siena; Liliana Gila; Antonio Proto, both of Novara, all of Italy

[73] Assignee: Enichem S.p.A., Milan, Italy

[21] Appl. No.: 08/802,875

[22] Filed: Feb. 19, 1997

[30] Foreign Application Priority Data

Feb. 22, 1996 [IT] Italy .................. MI96A0331

[51] Int. Cl.$^6$ ............ C08F 4/642; C08F 10/02; C07F 17/00
[52] U.S. Cl. ............ 526/160; 526/126; 526/127; 526/129; 526/130; 526/133; 526/134; 526/154; 526/156; 526/170; 526/352; 526/904; 526/943; 556/11; 556/13; 556/15; 556/20; 556/28; 556/52; 556/53; 502/103; 502/117; 502/120; 502/152; 502/153; 502/154; 502/155
[58] Field of Search ............ 526/160, 170, 526/126, 127, 129, 130, 134, 156, 154, 904, 943; 502/152, 103, 117, 120, 153, 154, 155; 556/11, 52, 13, 15, 20, 28, 53

[56] References Cited

U.S. PATENT DOCUMENTS 5,571,880  11/1996  Alt et al. .................. 526/160
5,631,202  5/1997   Ewen ...................... 526/160 X

FOREIGN PATENT DOCUMENTS 0 540 108 A1  5/1993  European Pat. Off. .
0 577 581 A2  1/1994  European Pat. Off. .
0 653 433 A1  5/1995  European Pat. Off. .
WO 95/25757  9/1995  WIPO .

*Primary Examiner*—Fred Teskin
*Attorney, Agent, or Firm*—Oblon, Spivak, McClelland, Maier & Neustadt, P.C.

[57] ABSTRACT

Metallocene complexes of a metal M selected from titanium, zirconium and hafnium, comprising at least one anionic group A containing an $\eta^5$-cyclopentadienyl ring co-ordinated with the metal M, wherein the anionic group is substituted in at least one position of the cyclopentadienyl ring with a radical having the formula:

$$Ph^* - (CR^6R^7)_n$$

wherein: $R^6$ and $R^7$ are independently hydrogen, halogen or a $C_1$–$C_4$ alkyl group, preferably hydrogen, "n" is 0 or 1, preferably 1, Ph* is a $C_6$–$C_{14}$ group comprising an aromatic ring linked to —$CR^6R^7$— or to A and substituted with at least one and up to a maximum of three electron-attractor groups, on the condition that, when A is an $\eta^5$-indenyl group and "n" is 0, at least one Ph group is linked to A in position 1 or 3 of indenyl.

These complexes can be used in (co)polymerization processes of α-olefins, possibly in the presence of a suitable co-catalyst, for the production of polyolefins with a very high molecular weight.

27 Claims, No Drawings

SUBSTITUTED METALLOCENE CATALYST FOR THE (CO)POLYMERIZATION OF OLEFINS

The present invention relates to a substituted metallocene catalyst for the (co)polymerization of olefins.

More specifically, the present invention relates to a substituted inetallocene complex of a metal of group 4 of the periodic table of elements, and a catalyst suitable for polymerizing or copolymerizing ethylene and/or other α-olefins, consisting of this catalyst combined with an appropriate co-catalyst. The present invention also relates to a process for the polymerization of α-olefins in the presence of this catalyst to obtain polyolefins with high molecular weights.

It is generally known in the art that ethylene, or alpha-olefins in general, can be polymerized by processes at low or medium pressure with catalysts based on a transition metal, generally known as catalysts of the Ziegler-Natta type. More recently, a particularof these catalysts which are active in the polymerization of olefins, has been found, consisting of a combination of an organic oxyderivative of aluminium (commonly called aluminoxane) with an $\eta^5$-cyclopentadienyl derivative of a metal normally selected from titanium, zirconium or hafnium (group 4 of the periodic table), also commonly called metallocene, definable in its more general form with the following formula (I):

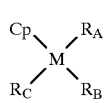

(I)

wherein M represents a metal of group 4 of the periodic table of elements, formally in the oxidation state +4, and is preferably titanium or zirconium; $R_A$ and $R_B$ each independently represent a group of an anionic nature such as, for example, a hydride, a halide, a phosphonated or sulfonated anion, an alkyl or alkoxy group, an aryl or aryloxy group, an amide group, a silyl group, etc.; Cp independently represents a ligand of the $\eta^5$-cyclopentadienylic type and is generally selected from $\eta^5$-cyclopentadienyl, $\eta^5$-indenyl, $\eta^5$-fluorenyl and their derivatives variously substituted; $R_C$, independently of the nature of the other substituents, can have one of the meanings of either the ligand Cp, or the $R_A$ or $R_B$ groups. Particular "bridged" metallocenes are also known in the known art, wherein two Cp groups, the same or different, are bound by a divalent radical normally containing at least one carbon atom, and possibly also heteroatoms such as, for example, nitrogen, oxygen, silicon or germanium. For a typical example of a known method for the preparation of the above compounds, reference should be made, as an example, to the description of H. Sinn, W. Kaminsky, in Adv. Organomet. Chem., vol. 18 (1980), page 99 and to U.S. Pat. No. 4.542.199.

These catalysts generally have a high catalytic activity and a certain versatility when applied to the preparation of polyolefins with specific characteristics, especially with respect to the control of the molecular weight dispersion, normally more limited than the classical Ziegler-Natta catalysts, or the stereoselectivity during the polymerization of α-olefins, normally obtained using the above "bridged" metallocene complexes.

It has been observed however that the behavior of the metallocene complexes is not entirely satisfactory with respect to the average molecular weight of the polyolefins obtained therewith, especially when operating with processes at a high temperature, and particularly in the copolymerization of ethylene with α-olefins to produce linear low density polyethylene (LLDPE) or olefinic elastomers (EPC). On the other hand, there is a great necessity for polymerization processes capable of producing polyolefins with the highest possible molecular weight to be able to develop different grades of product by intervening with suitable chain transfer agents.

It is also desirable to have catalysts based on metallocene complexes with a greater thermal stability and stability to reactive agents such as air or humidity, to simplify the conservation and transfer methods and operations of the complexes themselves.

Different types of variously substituted $\eta^5$-cyclopentadienyl binders have been examined in the known art, to improve the characteristics of the catalysts in relation to the specific applications and to overcome the above problems.

Published European patent application 576.970 describes particular bridged bis-indenyl complexes of zirconium, in which the benzene ring of each indenyl group is substituted with a phenyl or naphthyl group. Although the use of these complexes for the stereospecific polymerization of propylene is described, no important effect is mentioned with respect to the possible presence of substituents on the phenyl or naphthyl group.

Published European patent application 277.004 mentions metallocene complexes of group 4 of the periodic table, particularly zirconium, in which the cyclopentadienyl group is substituted with different radicals such as, for example, methyl, phenyl, benzyl, cyclohexyl or trifluoromethyl. The different substituents however are mentioned in general, without specifying any difference in their behavior when the complexes containing them are used in polymerization catalysis.

U.S. Pat. No. 5.324.800 discloses the use of bis-(2-phenylpropyl) cyclopentadienylzirconium dichloride in the polymerization of ethylene. A satisfactory activity of the catalyst is only obtained however when using very high quantities of methylaluminoxane, inacceptable for many industrial uses.

Published international patent application WO 95/25.757 describes bis-(2-phenyl)indenyl catalysts for the preparation of elastomeric block polypropylene. The characteristic of these catalysts is that they have a rotation rate of the ligands on the metallo-cyclopentadiene axis which is intermediate between the insertion rate of the monomer and the chain transfer rate, so as to produce adjacent blocks of isotactic and atactic polypropylene respectively. There seems to be no indication in this document as to the role of the substituents on the ligand in relation to the stability of the complex and molecular weight of the polymer produced therewith.

The demand for metallocene catalysts capable of basically overcoming all the various problems mentioned above, has therefore not as yet been satisfied.

The Applicant has now found a new group of catalysts for the (co)polymerization of α-olefins, based on metallocene complexes substituted on the cyclopentadienyl ring with particular groups of an electron-attractor nature, which can be prepared with simple and convenient synthetic methods. These complexes have greater chemical and thermal stability compared to analogous non-substituted complexes, and are active, possibly in the presence of a suitable co-catalyst, in the catalysis of (co)polymerization processes of α-olefins, to produce (co)polymers with very high molecular weights.

A first object of the present invention therefore relates to a metallocene complex of a metal M selected from titanium, zirconium and hafnium, comprising at least one anionic group A containing an η⁵-cyclopentadienyl ring co-ordinated with the metal M, characterized in that the anionic group is substituted in at least one position of the cyclopentadienyl ring with a radical having the formula:

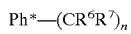

wherein: $R^6$ and $R^7$ are independently hydrogen, halogen or a $C_1$–$C_4$ alkyl group, preferably hydrogen or alkyl, more preferably hydrogen, "n" is 0 or 1, preferably 1, and Ph* is a $C_6$–$C_{14}$ group comprising an aromatic ring linked to —CR⁶R⁷— or to A and substituted with at least one and up to a maximum of three electron-attractor groups different from chlorine, on the condition that, when A is an η⁵-indenyl group and "n" is 0, at least one Ph* group is linked to A in position 1 or 3 of indenyl.

A second object of the present invention relates to a catalyst for the (co)polymerization of α-olefins, comprising the above metallocene complex, possibly in contact with a co-catalyst consisting of an organooxygenated derivative of a metal M' selected from aluminium, gallium and tin.

A further object of the present invention relates to a process for the (co)polymerization of α-olefins, comprising polymerizing ethylene and/or one or more α-olefins, under suitable conditions of pressure and temperature, in the presence of the above catalyst.

Any possible further objects of the present invention are evident from the following description and examples.

The term "(co)polymerization of α-olefins" as used hereafter in the description and claims, refers to both the homo-polymerization and co-polymerization of ethylene and/or other α-olefins with more than two carbon atoms, with each other or with another ethylenically unsaturated polymerizable compound.

Electron-attractor groups which are suitable as substituents of the aromatic ring of the Ph* group according to the present invention, are aprotic groups capable of polarizing the "π" orbitals of the aromatic ring with movement of the negative charge towards the substitution site. Electron-attractor groups of this type are fluorine atoms, halogenated hydrocarbon radicals, preferably fluorinated, having from 1 to 15 carbon atoms, halogenated alkylsilyl radicals, preferably fluorinated, having from 1 to 15 carbon atoms, alkoxy-carbonyl radicals, halogenated or non-halogenated, having from 2 to 15 carbon atoms, alkoxy- or aryloxy-alkyl radicals having from 2 to 15 carbon atoms, such as methoxymethyl, ethoxymethyl or trifluoromethyloxymethyl.

The electron-attractor groups present on the metallocene complexes of the present invention are preferably fluorine and the halogenated aliphatic hydrocarbyl or alkyl-silyl-radicals in which at least one halogen atom, preferably fluorine, is linked to a carbon atom or to a silicon atom in position 1 or 2 with respect to the aromatic ring of said Ph* group. Typical but non-limiting examples of these electronattractor groups are trifluoromethyl, difluoromethyl, fluorodichloromethyl, trichloromethyl, 1,1-difluoroethyl, 1,1-difluoropropyl, perfluoroethyl, 1,1-difluorohexyl, trifluoromethylsilyl, trifluorosilyl, trichloromethyldifluorosilyl, acetyl, trifluoroacetyl, perfluoropropionyl, trichloroacetyl and trifluoromethoxymethyl. Trifluoromethyl and perfluoroethyl are particularly preferred.

Aromatic rings included in the definition of the Ph* groups of the present invention are the benzene ring and naphthalene groups, preferably disubstituted with two electron-attractor groups defined above. Typical examples of Ph*—(CR⁶R⁷)ₙ groups according to the present invention, with $R^6$ and $R^7$ equal to hydrogen, are fluorobenzyl, difluorobenzyl, 4-trifluoromethylbenzyl, 2,4-bis-(trifluoromethyl)benzyl, 3,5-bis-(trifluoromethyl)benzyl, fluorophenyl, 4-trifluoromethylphenyl, 2,4-bis-(trifluoromethyl)phenyl, 3,5-bis-(trifluoromethyl)phenyl, 4-perfluoroethylbenzyl, 3,5-bis-(perfluoroethyl)benzyl, 3,5-bis-(perfluorobutyl)benzyl.

Typical metallocene complexes in accordance with the present invention are those represented by the following formula (II):

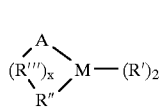

wherein: M represents a metal selected from titanium, zirconium or hafnium; each of the two R' independently represents a substituent group selected from hydride, halide, a $C_1$–$C_6$ alkyl group, a $C_3$–$C_{12}$ alkylsilyl group, a $C_5$–$C_8$ cycloalkyl group, a $C_6$–$C_{10}$ aryl group, a $C_1$–$C_8$ alkoxyl group, a $C_1$–$C_8$ carboxyl group, a $C_2$–$C_{10}$ dialkylamide group and a $C_4$–$C_{20}$ alkylsilylamide group;

R" represents a substituent group of the same kind as the previous R' groups, independently selected from these, or a second anion containing an η⁵-cyclopentadienyl ring substituted or non-substituted, co-ordinated to the metal M, possibly selected from the substituted cyclopentadienyl anions included in the following definition of A;

R'" represents a divalent group having from 1 to 10 carbon atoms, possibly containing one or more heteroatoms, preferably O, N, P, Sn, Ge or Si, which is bridge-linked between A and R" with covalent bonds, and R'" is preferably selected from alkylene, dialkylsilylene, diarylsilylene, dialkyl- or diarylgermylene, arylene, xylylene radicals and the like;

A is an anion containing a substituted η⁵-cyclopentadienyl ring, co-ordinated to the metal M, represented by the following formula (III):

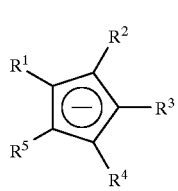

wherein: each $R^i$ group (with i=1, 2, 3, 4 or 5) can be independently hydrogen, halogen, a $C_1$–$C_8$ alkyl group, a $C_3$–$C_{12}$ alkylsilyl group, a $C_5$–$C_8$ cycloalkyl group, a $C_6$–$C_{14}$ aryl group, a $C_6$–$C_{15}$ arylalkyl group, a $C_1$–$C_8$ alkoxyl group, a $C_1$–$C_8$ carboxyl group, or two $R^i$ adjacent groups can combine with each other to form a cyclic aliphatic or aromatic structure comprising at least three, and preferably from 5 to 8 non-metallic atoms different from hydrogen and halogen; and "x" can be 0 or 1, on the condition that when "x" is 1, the divalent R'"group is linked on one side to the A group as a substitute of one for the $R^i$ groups having formula (III), and on the other side to the R" group, as a substitute for any of its hydrogen atoms;

characterized in that at least one $R^i$ in formula (III) of the A group, and possibly also in the formula of the R" group, when this is represented by formula (III), consists of a radical having the formula:

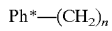

wherein: "n" and Ph* are defined as above, on the condition that, when A is an η⁵-indenyl group and "n" is 0, at least one Ph* group is linked to A in position 1 or 3 of indenyl.

According to the present invention, the R' groups having formula (II) can each independently represent, a hydride or halide, such as chloride or bromide, a $C_1$–$C_8$ alkyl group such as, for example, methyl, ethyl, butyl, isopropyl, isoamyl, octyl, benzyl, a $C_3$–$C_{12}$ alkylsilyl group such as, for example, trimethylsilyl, triethylsilyl or tributylsilyl, a cycloalkyl group such as cyclopentyl or cyclohexyl, a $C_6$–$C_{10}$ aryl group such as phenyl or toluyl, a $C_1$–$C_8$ alkoxyl group such as, for example, methoxyl, ethoxyl, iso- or sec-butoxyl, or a $C_2$–$C_{10}$ dialkylamide or $C_4$–$C_{20}$ alkylsilylamide group, preferably of the type represented by the general formula —$NR^8R^9$ wherein $R^8$ and $R^9$ are alkyl groups having from 1 to 4 carbon atoms, such as, for example, methyl, ethyl or butyl groups, or in the case of alkylsilylamides, alkylsilyl groups having from 3 to 6 carbon atoms, such as, for example, trimethylsilyl or triethylsilyl. The R' groups can also be joined to each other with a covalent bond to form a cyclic structure comprising the metal M. $(R')_2$ groups of this latter kind are, for example, 1,4-tetramethylene, ethylenedioxide or malonate groups.

Among the preferred R' groups in formula (II), chloride, methyl, benzyl and diethylamine radicals can be mentioned, although the scope of the present invention is by no means limited thereto.

In a particularly preferred embodiment the R' groups are the same as each other.

According to the present invention, the A group in formula (II) is an anion containing an η⁵-cyclopentadienyl ring having formula (III), which can be formally obtained by the extraction of a H⁺ ion from the cyclopentadienyl ring of the compound having the corresponding neutral molecular structure. Preferably, A represents an η⁵-cyclopentadiene group substituted with at least, and preferably one Ph*— $(CH_2)_n$ group, according to what is specified above, the remaining atoms in the ring being non-substituted, or substituted with $C_1$–$C_8$ alkyl or silylalkyl groups, or $C_6$–$C_{10}$ aryl or aryloxy groups, or $C_1$–$C_8$ alkoxyl groups. A is more preferably an η⁵-cyclopentadiene anion of formula (III) wherein $R^1$ is a Ph*—$CH_2$— group, particularly bis(fluoroalkyl)benzyl, and each of the remaining $R^2$, $R^3$, $R^4$ and $R^5$ are independently hydrogen or methyl.

The complexes and catalysts deriving from these however also fall within the scope of the present invention, in which group A is a cyclopentadienyl ring condenses with other cyclic structures, as in the case, for example, of the indenyl group, 4,5,6,7-tetrahydroindenyl or fluorenyl, as such or substituted as previously specified for non-condensed cyclopentadiene.

As previously defined, R" in formula (II) can represent either a group included in the above definiene group (generally indicated herein also with the abbreviation $C_P$) of the type commonly known in the art. More specifically, this $C_P$ group can represent an anion deriving from cyclopentadiene, indene or fluorene, or from a derivative of one of the above compounds, in which one or more carbon atoms of the molecular skeleton (comprised or not comprised in the cyclopentadienyl ring), are substituted with $C_1$–$C_8$ alkyl or silylalkyl groups, or $C_6$–$C_{15}$ aryl or aryloxy groups, or $C_6$–$C_{15}$ arylalkyl groups, or $C_1$–$C_8$ alkoxyl groups. This $C_P$ group can also be condensed with one or more other aromatic rings as in the case, for example, of 4,5-benzoindenyl.

Typical but non-limiting examples of these $C_P$ groups are cyclopentadienyl, indenyl, 4,5,6,7-tetrahydroindenyl, fluoroenyl groups and the corresponding methylsubstituted groups. However, complexes are preferred wherein the group R"=$C_P$ has a structure included in the previous definition of A, and is more preferably equal to A.

When "x"=1, the group R" is linked to the A group by the bridge R''', in which case it evidently represents a group comprised in the definition of R' or, respectively, $C_P$, but having a position substituted by the bond with the bridge R'''. When "x"=0, the A group and R" group are not linked to each other.

The group R''' can be, for example, 1,2-ethylene, ethylidene, 1,3-(2-methylidene)propylene, o-phenylene, m-phenylene, o-xylidene, m-xylidene, 1,4-butylene, 2-phenyl-1, 3-propylene, perfluoro-1, 3-propylene, dimethylsilylene, dimethylsilylenedimethylene, dimethylgermylenedimethylene, ethylenedioxy or dimethylsilylenedioxy.

Non-limiting examples of complexes having formula (II), suitable for the purposes of the present invention, are compounds having the formulae listed in table A below.

TABLE A

[η⁵-4-CF₃Bz)C₅H₄]₂TiCl₂
[η⁵-1-(4-CF₃Bz)THInd]₂ZrCL₂
[η⁵-(2,4-(CF₃)₂Bz)C₅H₄]ZrCl₂
[1,2-en(η⁵-1-(2,4-(CF₃)₂Bz)Ind)₂ZrCl₂
(η⁵-1(4-CF₃Bz)Ind)Zr(NMe₂)₃
[Me₂Si(CH₂)₂-(η⁵-(4-CF₃Bz)C₅H₃)₂]ZrCl₂
[Me₂Si(η⁵-(2,4-(CF₃)₂Bz)C₅H₃)₂]HfCl₂
[o-Xi-(η⁵-(2,4-(CF₃)₂Bz)C₅H₃)₂]ZrCl₂
[o-Xi-(η⁵-(4-CF₃Bz)THInd)₂ZrCl₂
[Prⁱ(η⁵-(4-CF₃Bz)C₅H₃)(η⁵-Flu)]ZrCl₂
[Me₂Si(η⁵-(4-CF₃Bz)C₅Me₃)(NBuᵗ)]TiCl₂
[η⁵-(2,4-(CF₃)₂Bz)C₅H₄]₂ZrCl(NMe₂)
[η⁵-(2,4-(CF₃)₂Bz)C₅Me₄]₂ZrMe₂
[η⁵-(4-CF₃Bz)C₅H₄]₂TiClMe
[1,2-en(η⁵-1-(2,4-(CF₃)₂Bz)THInd)₂ZrMe₂
[1,2-en(η⁵-1-(4-CF₃Bz)Ind)₂]TiMe₂
[η⁵-(3,5-(CF₃)₂Bz)C₅H₄]₂TiCl₂
[η⁵-1-(3,5-(CF₃)₂Bz)THInd]₂ZrCl₂
[η⁵-(3,5-(CF₃)₂Bz)C₅H₄]₂ZrCl₂
[η⁵-(4-FBz)C₅H₄]₂ZrCl₂
[1,2-en(η⁵-1-(3,5-(CF₃)₂Bz)Ind)₂]ZrCl₂
(η⁵-1-(3,5-(CF₃)₂Bz)Ind)Zr(NMe₂)₃
[Me₂Si(CH₂)₂-(η⁵-(3,5-(CF₃)₂Bz)C₅H₃)₂]ZrCl₂
[Me₂Si(η⁵-(3,5-(CF₃)₂Bz)C₅H₃)₂]HfCl₂
[o-Xi-(η⁵-(3,5-(CF₃)₂Bz)C₅H₃)₂]ZrCl₂
[0-Xi-(η⁵-(3,5-(CF₃)₂Bz)THInd)₂]ZrCl₂
[Me₂Si(η⁵-(3,5-(CF₃)₂Bz)C₅Me₃)(NBuᵗ)]TiCl₂
[η⁵-(3,5-(CF₃)₂Bz)C₅H₄]₂ZrCl(NMe₂)
[η⁵-(3,5-(CF₃)₂Bz)C₅Me₄]₂ZrMe₂
[η⁵-(3,5-(CF₃)₂Bz)C₅H₄]₂TiClMe
[1,2-en(η⁵-1-(3,5-(CF₃)₂Bz)THInd)₂ZrMe₂
[1,2-en(η⁵-1-(3,5-(CF₃)₂Bz)Ind)₂]TiMe₂
[η⁵-(3,5-(CF₃)₂Ph)C₅H₄]₂TiCl₂
[η⁵-(3,5-(CF₃)₂Ph)C₅H₄]₂ZrCl₂
[Me₂Si(CH₂)₂-(η⁵-(3,5-(CF₃)₂Ph)C₅H₃)₂]ZrCl₂
[Me₂Si(η⁵-(3,5-(CF₃)₂Ph)C₅H₃)₂]HfCl₂
[o-Xi-(η⁵-(3,5-(CF₃)₂Ph)C₅H₃)₂]ZrCl₂
[Me₂Si(η⁵-(3,5-(CF₃)₂Ph)C₅Me₃)(NBuᵗ)]TiCl₂

Also included in the scope of the present invention are mixtures of one or more metallocene complexes of the type previously defined. Catalysts of the present invention based on mixtures of these complexes can be advantageously used in polymerization when a wider molecular weight distribution of the polyolefins thus produced, is desired.

According to a particular form of embodiment, the complexes of the present invention can also be in a form supported on inert solids, preferably consisting of porous granular oxides of Si and/or Al, such as, for example, silica, alumina or silicoaluminates. Known supporting techniques can be used for the supporting of these complexes, normally comprising contact at temperatures of between room temperature and 100° C., in a suitable inert liquid medium, preferably hydrocarbon, between the carrier and complex in solution. Microspheroidal silica is particularly preferred for the supporting (average particle diameter 20–100 μm) having a BET surface area of between 150 and 700 m²/g, a total porosity >80% and an average pore radius of between 2 and 50 nm.

This inert solid can be subjected to an activation process before being used as a carrier to obtain a surface with a more suitable morphology and chemical composition. During the activation process the humidity and hydroxide groups present on the surface of the inert carrier are at least partially neutralized or eliminated up to a controlled and reproducible level.

For example, this activation process can consist in a treatment with a solution of an alkylderivative or an alkylhalide of a metal selected from metals of groups 1, 2 or 13 of the Periodic Table of Elements, such as a magnesium dialkyl, a magnesium alkylchloride, an aluminium trialkyl or an aluminium alkylchloride, in a liquid aliphatic hydrocarbon solvent, such as for example, pentane, isopentane, hexane, heptane and octane. It is convenient to operate with a quantity of this alkylderivative or alkyl-halide of between 10 and 25 parts by weight for every 100 parts by weight of granular carrier, putting the reagents in contact at a temperature of between −30 and 120° C., for times of between 0.5 and 5 hours, and preferably at a temperature of between 40 and 80° C., for times of from 1 to 2 hours. At the end of the treatment, the activated carrier is recovered, for example by filtration or decanting.

Alternatively, the granular carrier can be thermally activated, by heating in an inert atmosphere, to a temperature of between about 100° C. and about 800° C., for a time of between 1 and 20 hours. It is preferably to operate with a carrier activated by heating in an inert atmosphere (nitrogen) to a temperature of about 600° C. for a time of approximately 6 hours.

The preparation of the above metallocene complexes having formula (II) can be carried out with any of the known methods of organometallic chemistry, starting from a salt of the metal X and a cyclopentadienyl ligand having the desired structure. More generally, this ligand has the general formula (IV):

HA—(R''')$_x$—R''H         (IV)

wherein "x" A, R''' and R'' all have the general meaning previously specified for the complexes having formula (II).

For example, according to one of the above methods, the preparation of complexes having formula (II) comprises two steps, in the first of which the cyclopentadienyl binder is reacted with a lithium alkyl or lithium butyl, in an inert solvent preferably consisting of an aromatic hydrocarbon or an ether, particularly tetrahydrofuran or ethyl ether. The temperature during the reaction is preferably maintained below room temperature to avoid the creation of secondary reactions. At the end of the reaction the corresponding lithium salt of the cyclopentadienyl anion is obtained.

In the second step, the salt of the cyclopentadienyl anion is reacted with a salt, preferably a chloride, of the transition metal M, again in an inert organic solvent and at a temperature which is preferably lower than room temperature. At the end of the reaction the complex having formula (I) is separated and purified according to the known methods of organometallic chemistry.

Numerous general methods are described in literature specifically for the preparation of metallocene complexes, which basically correspond to the process described above. These methods, all well-known to experts in the field, can be generally used for the preparation of the complexes of the present invention, when the binder comprises, on at least one cyclopentadienyl ring, the particular aromatic groups with electron-attractor substituents described above. Methods of this type described in literature are, for example, those indicated in the publications of D. J.Cardin "Chemistry of Organo Zr and Hf compounds" J.Wiley and Sons Ed., New York (1986); R.Halterman "Chemical Review", vol.92 (1992) pages 965–994; R. O.Duthaler and A.Hafner "Chemical Review", vol.92 (1992) pages 807–832.

The cyclopentadienyl ligand having formula (IV), substituted with benzyl or phenyl groups comprising electron-attractor groups linked to the aromatic ring, can normally be obtained with the known methods of organic synthesis. It can be synthesized, for example, by the "coupling" reaction between the cyclopentadienyl salt of an alkaline metal, preferably sodium, and a chloride of the desired benzyl group. Or an "addition" reaction can be used between an alkaline salt of a phenyl or benzyl anion having the formula of the desired substituent, and a cyclopentenone to form the corresponding hydroxyderivative which is then dehydrated to obtain the substituted cyclopentadiene. An example of the reaction scheme for this latter process is subsequently shown in example 4, for the particular case of the synthesis of 3,5-bis-(trifluoromethyl)phenylcyclopentadiene. Ligands comprising naphthyl or naphthylmethyl groups, substituted with electronattractor groups can be synthesized with analogous processes.

A second object of the present invention relates to a catalyst for the (co)polymerization of α-olefins comprising the above substituted metallocene complex, or its cationic form obtained by the extraction therefrom of a non-cyclopentadienyl ligand of an anionic nature, particularly one of the R' groups of the complex having formula (II).

In a first embodiment, this catalyst of the present invention comprises, as well as the above complex, at least one co-catalyst consisting of an organo-oxygenated derivative of a metal M' selected from aluminium, gallium and tin. This can be defined as a compound in which the metal is linked to at least one oxygen atom and at least one organic $R^{10}$ group, wherein $R^{10}$ is $C_1$–$C_{10}$ hydrocarbyl, linear or branched. $R^{10}$ is preferably a linear $C_1$–$C_4$ alkyl, even more preferably methyl.

In accordance with the present invention, the cocatalyst is preferably an aluminoxane, more preferably methylaluminoxane.

As is known, aluminoxanes are compounds containing Al-O-Al bonds, with a variable O/Al ratio, which can be obtained in the art by the reaction, under controlled conditions, of an aluminium alkyl, or aluminium alkyl halide, with water or other compounds containing controlled quantities of water available, as for example, in the case of aluminium trimethyl, with a salt hydrate, such as aluminium hexahydrate sulfate, copper pentahydrate sulfate and iron pentahydrate sulfate. The aluminoxanes preferably used for the formation of the polymerization catalyst of the present invention are oligo- or poly-meric compounds, cyclic and/or linear, characterized by the presence of repetitive units having the formula:

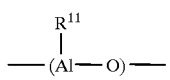

wherein $R^{11}$ is a $C_1$–$C_4$ alkyl group, preferably methyl.

Each molecule of aluminoxane preferably contains from 4 to 70 repetitive units which may not all be equal to each other, but contain different $R^{11}$ groups.

In addition to the above aluminoxanes, the definition of the co-catalyst of the present invention also comprises galloxanes (in which in the previous formulae, gallium is present instead of aluminium) and stannoxanes, whose use as polymerization co-catalysts of olefins in the presence of metallocene complexes is described, for example, for stannoxanes, in patents U.S. Pat. No. 5.128.295 and U.S. Pat. No. 5.258.475.

In the (co)polymerization catalysts of ethylene and α-olefins of the present invention, the metallocene complex and the co-catalyst can be used in such proportions that the atomic ratio between the metal M and the metal M' is in the range of 10 to 10000 and preferably from 200 to 5000. They are put in contact with each other with different procedures depending on the specific requirements of the polymerization process in which they are used. In particular the preparation of the polymerization catalyst of the present invention can be carried out by adding the metallocene complex to the (co)catalyst or viceversa. In addition, the mixing of the two components can be carried out with satisfactory results both before introducing the olefin to be polymerized and in the presence of said olefin.

In a second embodiment, the catalyst of the present invention is an ionic adduct in which the metallocene forms the cation, which can be obtained, for example, by the extraction reaction of a suitable group sigma-bonded to the metal M in a complex having the previous formula (II). These reactions preferably take place in an inert liquid medium, preferably hydrocarbon, and are normally carried out by putting a complex having formula (II) in contact with a suitable co-catalyst (C) consisting of a compound, or a combination of compounds, capable of activating the formation of the cationic species.

This co-catalyst is preferably selected from non-protic Lewis acids capable of extracting a sigma-bonded anionic group from this neutral metallocene complex to form a non-co-ordinating anion, and organic salts whose anion is non-co-ordinating and whose cation is capable of extracting a sigma-bound anionic group from this neutral metallocene complex to form a neutral compound. Typical examples of organic salts are the tetra(perfluoro)arylborates of dialkylanilinium or triarylcarbenium. Typical examples of Lewis acids are tris(perfluoroiaryl)-boranes or -borates.

According to a particular aspect of the present invention, when the metallocene complex does not comprise alkyl or amidic R' groups linked to the metal M, it is first interacted with a suitable alkylating agent, such as an alkyl-magnesium or an alkyl-aluminium, and subsequently combined with the co-catalyst (C) to form the catalyst of the present invention.

Examples of the above formation reactions of the cationic species are qualitatively schematized in the list below, which however does not limit the scope of the present invention:

i) by the reaction of a metallocene having the previous general formula (II), in which, preferably, at least one of the R' groups is an anion of a weak acid, more preferably alkyl, aryl or dialkylamide, with an ionic compound whose cation is capable of extracting this R' group to form a neutral compound, and whose anion is non-coordinating, such as, for example, triphenylcarbenium tetrakis-(pentafluorophenyl)borate or dimethylanilinium tetrakis (pentafluorophenyl)borate;

ii) by the reaction of any non-ionic metallocene complex of the present invention, preferably having the previous formula (II), with an alkylating agent, preferably a magnesium dialkyl or an aluminium trialkyl, used in molar excess 5–50/1, followed by the reaction with a strong aprotic Lewis acid, such as, for example, tris (pentafluorophenyl)boron, in a practically stoichiometric quantity with the metal M;

iii) by the reaction of a metallocene having the previous formula (II), in which at least one R'group is alkyl or alkylene, with an almost stoichiometric quantity or in slight excess of a strong Lewis acid, such as, for example, tris(pentafluorophenyl)boron. The above reactions, and possibly others not included in those listed above, for the formation of cationic metallocene complexes capable of polymerizing α-olefins, without the necessity of using a great excess of co-catalyst such as an aluminoxane, are generally described in literature and known to experts in the field.

As an example, for the description of suitable cocatalysts (C) and processes for the formation of cationic metallocenes, reference can be made to the publications of R. R.Jordan in "Advances in Organometallic Chemistry", vol. 32 (1990), pages 325–387, and X.Yang et al. in "Journal of the American Chemical Society", vol. 116 (1994), page 10015, as well as the following patent publications:

European patent applications published with the Nr. EP-A 522.581, EP-A 495 375, EP-A 520732, EP-A 478913, EP-A 468651, EP-A 427697, EP-A 421659, EP-A 418044;

International applications published with the Nr.: WO 92/00333; WO 92/05208;

U.S. Pat. Nos.: 5,064,802, 2,827,446, 5,066,739.

Non-limiting examples of ionic metallocene derivatives which can be used as catalysts of the present invention are listed below in table B, with reference to the respective precursors from whose combination they are obtained:

TABLE B

| Metallocene | Co-Catalyst (C) |
|---|---|
| [o-Xi-($\eta^5$-(3,5-$(CF_3)_2$Bz)$C_5H_3$)$_2$]ZrCl$_2$ | |
| [$\eta^5$-1-(3,5-$(CF_3)_2$Bz)THInd]$_2$ZrMe$_2$ | $B(C_6F_5)_3$ |
| [o-Xi-($\eta^5$-(4-$CF_3$Bz)$C_5H_3$)$_2$]ZrMe$_2$ | $(MeNHPh)^+[B(C_6F_5)_4]^-$ |
| [$\eta^5$-(3,5-$(CF_3)_2$Bz)$C_5Me_4$]$_2$ZrMe$_2$ | $(Ph_3C)^+[B(C_6F_5)_4]^-$ |
| [$\eta^5$-(3,5-$(CF_3)_2$Bz)$C_5H_4$]$_2$TiClMe | |
| [1,2-en($\eta^5$-1-(2,4-$(CF_3)_2$Bz)THInd)$_2$]ZrMe$_2$ | |

TABLE B-continued

| Metallocene | Alkylating agent | Co-catalyst (C) |
|---|---|---|
| [$\eta^5$-(2,4-(CF$_3$)$_2$Bz)C$_5$H$_4$]$_2$TiCl$_2$ | | |
| [$\eta^5$-1-(3,5-(CF$_3$)$_2$Bz)THInd]$_2$ZrCl$_2$ | | |
| [$\eta^5$-(3,5-(CF$_3$)$_2$Bz)C$_5$H$_4$]$_2$ZrCl$_2$ | | |
| [1,2-en($\eta^5$-1-(2,4-(CF$_3$)$_2$Bz)Ind)$_2$]ZrCl$_2$ | | |
| [$\eta^5$-1-(3,5-(CF$_3$)$_2$Bz)Ind]Zr(NMe$_2$)$_3$ | | |
| [Ph$_2$Si($\eta^5$-1-(2,4-(CF$_3$)$_2$Bz)C$_5$H$_3$)$_2$]ZrCl$_2$ | AlBu$_3^i$ | B(C$_6$F$_5$)$_3$ |
| [Me$_2$Si($\eta^5$-1-(2,4-(CF$_3$)$_2$Bz)Ind)$_2$]HfCl$_2$ | AlEt$_3$ | (Ph$_3$C)$^+$[B(C$_6$F$_5$)$_4$]$^-$ |
| [o-Xi-($\eta^5$-(3,5-(CF$_3$)$_2$Bz)C$_5$H$_3$)$_2$]ZrCl$_2$ | AlMe$_3$ | (Me$_2$NHPh)$^+$[B(C$_6$F$_5$)$_4$]$^-$ |
| [o-Xi-($\eta^5$-(4-CF$_3$Bz)C$_5$H$_3$)$_2$]ZrC$_2$ | | |
| [o-Xi-($\eta^5$-(3,5-(CF$_3$)$_2$Bz)THInd)$_2$]ZrCl$_2$ | | |
| [Me$_2$Si($\eta^5$-(2,4-(CF$_3$)$_2$Bz)C$_5$Me$_3$)(NBu$^t$)]TiCl$_2$ | | |
| [$\eta^5$-(3,5-(CF$_3$)$_2$Bz)C$_5$H$_4$]$_2$ZrCl(NMe$_2$) | | |

Abbreviations: Ph = phenyl, o-Xi = ortho-xylylene, Me = methyl, Et = ethyl, Bu$^t$ = tert-butyl, Bu$^i$ = iso-butyl, Bz = benzyl, Pr$^i$ = 2,2-isopropylidene, Me$_2$Si = dimethylsilylene, Ind = indenyl, THInd = 4.5.6.7-tetrahydroindenyl, 1,2-en = 1,2-ethylidene, Ph$_2$Si = diphenylsilylene.

Also included in the scope of the present invention are those catalysts comprising, as well as the etallocene complex of the present invention, in a neutral or ionic form, a solid, granular polymeric carrier, either inorganic or organic, preferably selected from inert inorganic oxides of the type previously described, more preferably selected from alumina, silica and silicoaluminates. These supported catalysts can, for example, be obtained with one of the known supporting techniques, normally comprising contact, in a suitable inert liquid medium, between the solid carrier, possibly activated as described above, and one or both of the components of the catalyst of the present invention, i.e. the metallocene complex and/or the co-catalyst. It is not necessary, for the purposes of the present invention, for both of these components to be supported, as the metallocene complex alone, preferably having formula (II), or the co-catalyst, preferably an aluminoxane, can also be present on the surface of the carrier. In the latter case the component which is not on the surface is subsequently put in contact with the supported component, at the moment when the active catalyst for the polymerization is required.

One or more other additives can possibly be added to the catalyst of the present invention, or to the metallocene complex alone or the co-catalyst alone, before contact with the other component, to obtain a catalytic system which is suitable for satisfying specific requisites in the embodiment. In any case, these catalytic systems are also included in the scope of the present invention. Additives or components which can be included in the preparation and/or formulation of the catalyst of the present invention are inert solvents, such as, for example, aliphatic and/or aromatic hydrocarbons, aliphatic and aromatic ethers, weakly co-ordinating additives (Lewis bases) selected, for example, from ethers, tertiary amines and alcohols, halogenating agents such as silicon halides, halogenated hydrocarbons, preferably chlorinated, and similar products, and again all the other additional components normally used in the preparation of traditional homogeneous and heterogeneous catalysts of the metallocene type for the (co)polymerization of ethylene and α-olefins.

The catalysts of the present invention can be used with excellent results in basically all of the known (co) polymerization processes of α-olefins, such as, for example, processes in suspension, at low, medium or high pressure and at temperatures of between 50 and 240° C.; processes in solution in an inert diluent operating at pressures of between 10 and 150 bars and temperatures of between 120 and 230° C.; or in a gas phase, with temperatures generally within the range of 60 to 160° C., at pressures of between 5 and 50 bars. The polymers or copolymers thus obtained have very high average molecular weights, even if the processes used operate at a high temperature. If the molecular weight is to be regulated to a value which is lower than the maximum value obtainable, it is possible to use a chain transfer agent, such as, for example, hydrogen, as known in the art.

According to a particular aspect of the present invention, the catalyst for the (co)polymerization of α-olefins is prepared separately by contact of the metallocene complex with a suitable co-catalyst, preferably methylaluminoxane, and subsequently introduced into the polymerization environment. The catalyst can be introduced first into the polymerization reactor, followed by the reagent mixture containing the olefin or the mixture of olefins to be polymerized, or the catalyst can be introduced into the reactor already containing the reagent mixture, or, finally, the reagent mixture and the catalyst can be contemporaneously fed into the reactor.

According to another aspect of the present invention, the catalyst is formed in situ in the polymerization reactor, for example by first introducing an aluminoxane, subsequently the metallocene complex having formula (I), and finally feeding the olefinic monomer.

When the catalyst of the present invention is of the ionic type previously described, it is preferable to preform the catalyst, for example, using one of the above extraction reactions (i), (ii) or (iii), and introduce it subsequently into the polymerization reactor, before, after or contemporaneously with the α-olefin to be polymerized.

The catalysts of the present invention can be used with excellent results in the polymerization of ethylene to give linear polyethylene and in the copolymerization of ethylene with propylene or higher α-olefins to give copolymers with different characteristics depending on the specific polymerization conditions and the quantity and structure of the α-olefin itself. The catalyst of the present invention can also be conveniently used for the terpolymerization of ethylene, propylene and a diene to obtain vulcanizable rubbers of the EPDM type. Particularly in the case of the above copolymerization and terpolymerization processes of ethylene, the catalysts of the present invention enable the production of polymers having higher average molecular weights with respect to the traditional metallocene catalysts, under the same polymerization conditions and with the same quantity and type of comonomer inserted.

The present invention is further described in the following examples which however are purely illustrative and do not limit the scope of the invention itself.

The characterization by means of $^1$H-NMR spectroscopy, mentioned in the following examples, was carried out on a nuclear magnetic resonance spectrometer mod. Bruker MSL-200.

The measurement of the molecular weights was carried out by Gel-Permeation chromatography (GPC). The analyses of the polyethylene (PE) samples were carried out in 1,2,4-trichlorobenzene (stabilized with Santonox) at 135° C. with a WATERS 150-CV chromatograph using a Waters differential refractometer as detector.

The chromatographic separation was obtained with a set of μStyragel HT columns (Waters) of which three with pore dimensions of 103, 104, 105 respectively, and two with pore dimensions of 106 Å, establishing a flow rate of the eluant of 1 ml/min. The data were received and processed with Maxima 820 software version 3.30 (Millipore); for the calculation of the number average molecular weight (Mn) and weight average molecular weight (Mw), the universal calibration principles were applied, selecting polystyrene standards for the calibration with molecular weights within the range of 6,500,000–2,000.

During the preparations described in the examples the commercial reagents listed below were used:

Methyllithium (MeLi) 1.6 M in diethyl ether ALDRICH
Butyllithium (BuLi) 2.5 M in hexane ALDRICH
Fluorobenzyl chloride ALDRICH
p-trifluoromethylbenzylchloride FLUKA
2,4-bistrifluoromethylbenzyl chloride ALDRICH
3,5-bis-trifluoromethyl-1-bromobenzene FLUKA
Zirconium tetrachloride (ZrCl$_4$) FLUKA
Methylalumoxane (MAO) 1,5 M in toluene WITCO The reagents and/or solvents used in the following examples and not indicated above are those normally used and can be easily found on the market by any expert in the field.

EXAMPLE 1

Synthesis of the complex bis-[η$^5$-(4-fluorobenzyl) cyclopentadienyl]-zirconi-umdichloride 1) Preparation of 4-fluorobenzylcyclopentadiene 10 ml of a suspension at 30% by weight of metal sodium in toluene are added to a 500 ml glass flask, equipped with a cooler, drip-funnel, tap for the inlet of argon and magnetic stirring, containing 200 ml of anhydrous tetrahydrofuran (THF). 12 ml of freshly distilled cyclopentadiene are added drop-wise to the suspension, obtaining a limpid, colourless solution. The solution is then cooled to 5–10° C. and 7.7 g of fluorobenzyl chloride (54 mmoles) are added. During the addition there is the formation of a precipitate of NaCl. The mixture is left under stirring for 2 hours, and 50 ml of water are then added. The mixture is then extracted with two portions of 50 ml of petroleum ether and the organic phase separated is concentrated to obtain an oily residue which is subsequently eluated on silica gel using petroleum ether as eluant. After evaporation of the eluant 3.5 g of pure product are obtained, which, after characterization by NMR spectroscopy proves to be 4-fluorobenzylcyclopentadiene (37% yield with respect to the fluorobenzyl chloride).

2) Preparation of 4-fluorobenzylcyclopentadienyl lithium 7 g of 4-fluorobenzylcyclopentadiene (40 mmoles) and 50 ml of hexane are charged, in an argon atmosphere, into a tailed test-tube equipped with magnetic stirring. The solution is cooled to 0° C. and 16 ml of a 2.4M solution of butyllithium in hexane are added. The temperature is then allowed to rise to room temperature and the mixture is left under stirring for a night. A precipitate is formed which is filtered, washed twice with 10 ml of hexane and finally dried. 6.5 g of the desired salt are obtained with a yield of 90%.

3) Preparation of the complex 0.4 g of 4-fluorobenzylcyclopentadienyl lithium (2.2 mmoles) and 20 ml of THF are introduced, in an argon atmosphere, into a tailed test-tube equipped with magnetic stirring. 0.414 g of ZrCl$_4$(THF)$_2$ (1.10 mmoles) previously dissolved in 30 ml of THF are added, under stirring, to the solution thus obtained. The stirring is maintained at room temperature for 48 hours. The mixture is concentrated to solidification and toluene is added to the solid; the undissolved part is filtered away and the solution is then concentrated until the product precipitates. At the end 0.18 g of white microcrystalline solid are obtained which, after characterization by NMR spectroscopy, proves to be bis-[η$^5$-(4-fluorobenzyl)-cyclopentadienyl]zirconiumdichloride, with a yield of 29%.

$^1$H-NMR spectrum (toluene D$^8$, ppm rel.to TMS) :6.85–6.72 (m); 6.1 (q,1H); 5.72 (q,1H); 5.48 (q,1H); 3.9 (d,2H)

EXAMPLE 2

Synthesis of bis-[η$^5$-(4-trifluoromethyl-benzyl) cyclopentadienyl]-zirconiumdichloride 1) Preparation of 4-trifluoromethylbenzylcyclopentadiene Exactly the same procedure is used as described in paragraph 1 of example 1 above, with the only difference that 10.5 g of p-trifluoromethylbenzylchloride (54 mmoles) are used instead of 7.7 g of fluorobenzyl chloride. At the end 5.1 g of pure product are obtained which, after characterization with NMR spectroscopy, proves to be 4-trifluoromethylbenzylcyclopentadiene (yield 42% with respect to the initial trifluoromethylcyclopentadiene).

2) Preparation of 4-trifluoromethylbenzylcyclopentadienyl lithium 2.5 g of 4-trifluoromethylbenzylcyclopentadiene (10 mmoles) and 30 ml of hexane are charged, in an argon atmosphere, into a tailed test-tube equipped with magnetic stirring. The same procedure is then carried out as in paragraph 2 of example 1 above, using 4.5 ml of a 2.5 M solution of butyllithium in hexane. At the end, 2.1 g of the desired salt are obtained with a yield of 80%.

3) Preparation of the complex 0.75 g of 4-trifluoromethylbenzylcyclopentadienyl lithium (2.6 mmoles) and 30 ml of THF are introduced, in an argon atmosphere, into a tailed test-tube equipped with magnetic stirring. 0.414 g of ZrCl$_4$(THF)$_2$ previously dissolved in 30 ml of THF are added, under stirring, to the solution thus obtained. The same procedure is then carried out as in paragraph 3 of example 1 above, obtaining at the end 0.512 g of white microcrystalline solid which after characterization by NMR spectroscopy proves to be bis-[η$^5$-(4-trifluoromethylbenzyl)cyclopentadienyl]-zirconiumdichloride, with a yield of 61%.

$^1$H-NMR spectrum (toluene D$^8$, ppm rel.to TMS):7.2–6.8 (m); 5.82 (t,2H); 5.6 (t,2H); 3.95 (s,2H).

EXAMPLE 3

Synthesis of bis-[η$^5$-(2,4-bistrifluoromethyl benzyl) cyclopentadienyl]-zirconiumdichloride 1) Preparation of 2,4-bistrifluoromethylbenzylcyclopentadiene 7 ml of a suspension at 30% by weight of metal sodium in toluene are added to a 500 ml glass flask, containing 100 ml of anhydrous tetrahydrofuran (THF). 9 ml of freshly distilled cyclopentadiene are added drop-wise to the suspension, maintained at a temperature lower than 30° C., obtaining a colourless solution.

The solution is then cooled to 0° C. and 20 g of 2,4-bistrifluoromethylbenzyl chloride (76 mmoles) are added. The temperature is left to rise to room temperature and the mixture is left under stirring for about 4 hours until the chloride disappears. 50 ml of water are then added, and the mixture is then extracted with two portions of 50 ml of petroleum ether. The organic phase separated is concentrated to obtain an oily yellow-colored residue (21 g), containing a mixture of cyclopentadiene mono- and di-substituted with the benzyl group. This residue is immediately distilled, collecting the fraction with a boiling point of 40° C. at 13.1 Pa. The product thus obtained (3.5 g, yield 14%) must be maintained in a solution of hexane at a temperature of 0° C. or less, to avoid dimerization, and it proved to consist of two isomers having the structures (V) and (VI) below, of which the $^1$H-NMR characterization is given

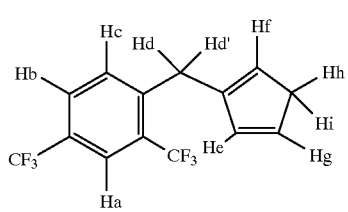

(V)

$^1$H-NMR spectrum (CDCl$_3$, ppm rel. to TMS): 7.85 (s, Ha); 7.26 (d, Hb, J=8.12 Hz); 6.99(6.89) (d, Hc, J=8.12 Hz); 5.95(5.76) (dq, He, $J_{Hg-He}$=4.56 Hz, $J_{He-Hh}$=2.66 Hz, $J_{He-Hi}$=1.36 Hz).

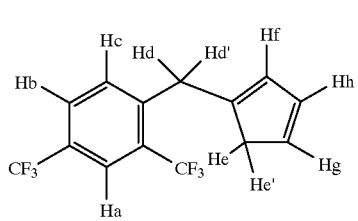

(VI)

$^1$H-NMR spectrum (CDCl$_3$, ppm rel. to TMS): 7.85 (s, Ha); 7.26 (d, Hb, J=8.12 Hz); 6.99(6.89) (d, Hc, J=8.12 Hz); 5.95(5.76) (dq, Hg, $J_{Hg-Hh}$=4.56 Hz, $J_{Hg-He}$=9.66 Hz, $J_{Hg-He'}$=1.36 Hz).

2) Preparation of 2,4-bistrifluoromethylbenzylcyclopentadienyl lithium 3.5 g of 2,4-bistrifluoromethylbenzylcyclopentadiene and 30 ml of hexane are charged, in an argon atmosphere, into a tailed test-tube equipped with magnetic stirring. 6 ml of a 2.5 M solution of butyllithium in hexane are then added. There is an immediate reaction with the development of heat and the formation of a yellow precipitate which is washed several times with hexane by decanting and finally dried. 3.0 g of the desired salt are obtained with a yield of 85%.

3) Preparation of the complex 1.0 g of 2,4-bistrifluoromethylbenzylcyclopentadienyl lithium (3.36 mmoles) in 40 ml of THF are introduced, in an argon atmosphere, into a tailed test-tube equipped with magnetic stirring. 0.60 g of ZrCl$_4$(THF)$_2$ (1.59 mmoles) are added, under stirring at 0° C., to the solution. The mixture is then left at room temperature for 8 hours. The solvent is evaporated under vacuum and the residue is extracted with 30 ml of toluene. The toluene phase is concentrated to about 15 ml, 3–4 ml of hexane are added and the mixture is left to rest. A crystalline solid is formed which after filtration and drying, has a weight of 0.7 g. The product after characterization by NMR spectroscopy, proves to be bis-[$\eta^5$-(2,4-bistrifluoromethylbenzyl)-cyclopentadienyl]-zirconiumdichloride, with a yield of 63%.

$^1$H-NMR spectrum (benzene D$^6$, ppm rel.to TMS): 7.75 (s, 2H); 7.20 (d, 1H); 7.05 (d, 1H); 5.85 (t,2H); 5.52 (t, 2H); 4.22 (s, 2H).

EXAMPLE 4

Synthesis of the complex bis-[$\eta^5$-(3,5-bis-trifluoromethylphenyl)-cyclopentadienyl] zirconiumdichloride (VII)

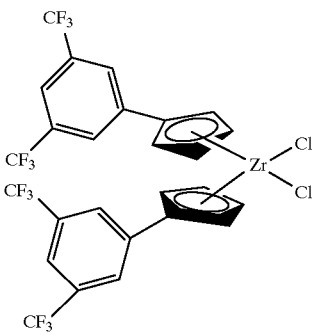

(VII)

1) Preparation of 3,5-bis-(trifluoromethylphenyl) cyclopentadiene

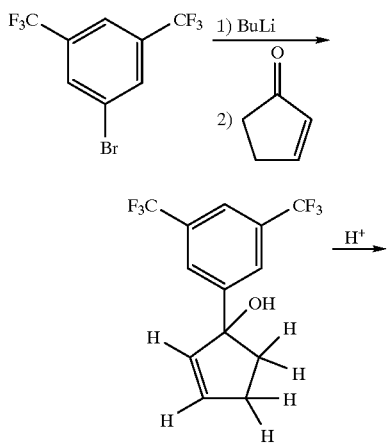

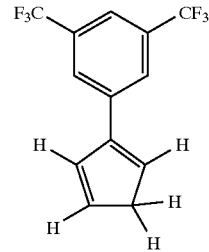

Reaction scheme 16 ml of a 2.5 M solution if butyllithium in hexane are added to a solution of 11.7 g of 3,5-bis-trifluoromethyl-1- bromobenzene (40 mmoles) in 100 ml of diethyl ether, maintained at −60° C. The mixture is left under stirring for 1 hour at a temperature of between −60 and −50° C. 5 ml of cyclopent-2-enone are then added and the temperature of the mixture is left to rise to room temperature, under stirring. About 50 ml of water are added and the mixture is extracted with diethyl ether. The organic extracts are dried on igroscopic salts and the solvent is evaporated. The oily residue is distilled under vacuum collecting the fraction with a boiling point of 65–67° C. at 13.1 Pa (0.1 mmHg), which solidifies at room temperature and consists of 3-hydroxy-3-(3,5-bis-trifluoromethyl) phenylcyclopentene at 98% of purity (gaschromatography).

5 g of this hydroxyderivative are dissolved in 150 ml of petroleum ether containing 10 g of anhydrous silica and 5 mg of p-toluenesulfonic acid. The suspension is left under stirring for 30 minutes until the disappearance of the reagent. The reaction product, consisting of 3,5-bis-(trifluoromethylphenyl)cyclopentadiene containing its dimer, is not isolated but is used immediately, in the form of a suspension for the subsequent preparation.

2) Preparation of 3,5-bis-trifluoromethylphenyl cyclopentadienyl lithium

The suspension obtained as in the previous paragraph is filtered on silica to separate the suspended solid. 3 ml of a 2.5 M solution of butyllithium in hexane are added to the limpid liquid, and the mixture is stirred for 2 hours with the formation of a precipitate which is separated by filtration, washed with hexane and dried under vacuum. 2.5 g of the desired salt are obtained.

3) Preparation of the complex

A solution of 2.0 g of 3,5-bistrifluoromethylphenylcyclopentadienyl lithium (7.0 mmoles) in 70 ml of THF is prepared in a tailed test-tube equipped with magnetic stirring. 1.32 g of $ZrCl_4(THF)_2$ (3.5 mmoles) are added, under stirring at 0° C., to the solution. The mixture is then left at room temperature for 24 hours. The solvent is evaporated under vacuum and the residue is extracted with toluene. The toluene phase is evaporated and the residue is extracted again with methylene chloride. On subsequent evaporation of $CH_2Cl_2$ from the extract, a white solid is formed which has a weight of 1.2 g, which after characterization by NMR spectroscopy, proves to be bis-[$\eta^5$-(3,5-bistrifluoromethylphenyl)-cyclopentadienyl] zirconiumdichloride, (yield of 50%).

$^1$H-NMR spectrum (CDCl$_3$, ppm rel.to TMS): 7.6 (Ar, 2H); 7.4 (Ar, 2H); 6.7 (m, 2H); 6.4 (m, 2H).

EXAMPLES 5–8

Polymerization of Ethylene

Various polymerization tests of ethylene were carried out corresponding to examples 5 to 8, using the following general procedure.

500 ml of toluene (previously distilled on metal sodium) and 0.54 ml of the above solution of MAO at 10% in toluene are charged into a BUCHI autoclave with a glass reactor having a volume of 1 litre, equipped with a propeller stirrer, thermocouple and heating jacket connected to a thermostat for the temperature control, maintained under vacuum for at least two hours interrupted by three washings with nitrogen. The pressure-resistant reactor is heated to 70° C. and the desired quantity of metallocene complex according to the present invention is introduced, with a syringe, so that the atomic ratio between the transition metal (in this case zirconium) in the complex and the aluminium introduced as MAO is equal to about 2500. The pressure-resistant reactor is pressurized with ethylene up to a pressure of 2 atms, and the polymerization is carried out for 30 minutes, continuously feeding the ethylene to maintain the pressure constant for the whole duration of the test. The polymer is recovered by precipitation in acidified methanol and subsequent washings with acetone. The polymer thus obtained is linear polyethylene (HDPE) which is characterized by measuring the number average molecular weight ($M_e$) and the weight average molecular weight ($M_u$) and the molecular weight distribution (MWD=$M_w/M_n$).

Different polymerization tests were carried out with the above procedure, using the complexes prepared according to the previous examples 1 to 4. The conditions and results of the polymerizations are summarized in Table 1, below, in which, for each example, the zirconium complex is identified in the second column with reference to the respective preparation example.

EXAMPLE 9

(comparative)

For comparative purposes a polymerization test of ethylene was carried out under the same conditions as the previous examples 5 to 8, but using bis-($\eta^5$-cyclopentadienyl)zirconium dichloride ($\eta^5$-$C_5H_5$)$_2$ZrCl$_2$, as metallocene complex. The results and characterization of the polyethylene thus obtained are shown in table 1.

TABLE 1

| | 18/28 Ethylene polymerization Zirconium complex | | | | | | |
|---|---|---|---|---|---|---|---|
| Example Nr | Reference example Nr | Quantity (mg) | Concentration (moles*10$^6$) | Yield (PE g) | Activity (g$_{PE}$/mg$_{Zr}$*hr) | Mn | MWD |
| 5 | 1 | 0.17 | 0.70 | 7.4 | 354 | 190,000 | 2.4 |
| 6 | 3 | 0.25 | 0.70 | 1.3 | 62 | 398,000 | n.m. |
| 7$^{(a)}$ | 3 | 0.40 | 1.10 | 5.8 | 220 | 311,000 | n.m. |
| 8 | 4 | 0.24 | 0.70 | 8.6 | 406 | 192,000 | 2.1 |
| 9 | ($\eta^5$-C$_5$H$_5$)$_2$ZrCl$_2$ | 0.10 | 0.70 | 6.9 | 326 | 142,000 | 2.3 |

$^{(a)}$Ethylene pressure = 10 Atm
n.m. = Not measured

We claim:

1. A metallocene complex represented by the following formula (II):

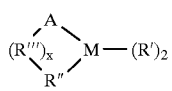
(II)

wherein:
M is a metal selected from the group consisting of titanium, zirconium and hafnium;
each of the two R' independently represents a substituent group selected from the group consisting of a hydride, a halide, a $C_1$–$C_8$ alkyl group, a $C_3$–$C_{12}$ alkylsilyl group, a $C_5$–$C_8$ cycloalkyl group, a $C_6$–$C_{10}$ aryl group, a $C_1$–$C_8$ alkoxy group, a $C_1$–$C_8$ carboxyl group, a $C_2$–$C_{10}$ dialkylamide group and a $C_4$–$C_{20}$ alkylsilylamide group;
R" is a divalent radical derived from a group selected from a $C_1$–$C_8$ alkyl group, a $C_3$–$C_{12}$ alkylsilyl group, a $C_5$–$C_8$ cycloalkyl group, a $C_6$–$C_{10}$ aryl group, a $C_1$–$C_8$ alkoxy group, a $C_1$–$C_8$ carboxyl group, a $C_2$–$C_{10}$ dialkylamide group or a $C_4$–$C_{20}$ alkylsilylamide group; or a second anion containing an $\eta^5$-cyclopentadienyl ring substituted or non-substituted, coordinated to the metal M,
R'" is a divalent group having from 1 to 10 carbon atoms, optionally containing one or more heteroatoms which is a bridge-linked between A and R" by covalent bonds,
A is an anion containing a substituted $\eta^5$-cyclopentadienyl ring, co-ordinated to the metal M, represented by the following formula (III):

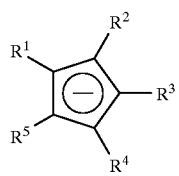
(III)

wherein: each of $R^1$, $R^2$, $R^3$, $R^4$ and $R^5$, independently, is hydrogen, halogen, a $C_1$–$C_8$ alkyl group, a $C_3$–$C_{12}$ alkylsilyl group, a $C_5$–$C_8$ cycloalkyl group, a $C_6$–$C_{14}$ aryl group, a $C_6$–$C_{15}$ arylalkyl group, a $C_1$–$C_8$ alkoxyl group, a $C_1$–$C_8$ carboxyl group, or two adjacent $R^1$, $R^2$, $R^3$, $R^4$ and $R^5$ groups combined with each other to form a cyclic aliphatic or aromatic structure comprising at least three non-metallic atoms different than hydrogen and halogen; and "x" is 0 to 1, with the proviso that when "x" is 1, the divalent R'" group is linked on one side to the A group in place $R^1$, $R^2$, $R^3$, $R^4$ or $R^5$, of formula (III), and on the other side to the R" group in place of its hydrogen atoms;
wherein at least one $R^1$, $R^2$, $R^3$, $R^4$ and $R^5$, in formula (III), optionally also in the R" group in formula (II), is a radical of the formula:

Ph*—CH$_2$— wherein Ph* is an aromatic $C_6$–$C_{14}$ group linked to A and substituted with at least one and up to a maximum of three electron-attractor groups other than chlorine.

2. A Metallocene complex according to claim 1, wherein the heteroatoms are O, N, P, Sn, Ge or Si.

3. Metallocene complex according to claim 1, wherein R" is as defined for A.

4. Metallocene complex according to claim 1, wherein the electron-attractor group is fluorine.

5. Metallocene complex according to claim 1, wherein Ph*—CH$_2$— is bis(fluoroalkyl)benzyl.

6. Metallocene complex according to claim 1, wherein the electron-attractor group on Ph* is selected from the group consisting of fluorine, halogenated hydrocarbon radicals having from 1 to 15 carbon atoms, halogenated alkylsilyl radicals having from 1 to 15 carbon atoms, alkoxycarbonyl radicals halogenated or non-halogenated having from 2 to 15 carbon atoms, and alkoxy-alkyl and aryloxy-alkyl radicals having from 2 to 15 carbon atoms.

7. Metallocene complex according to claim 1, wherein the electron-attractor group on Ph* is selected from the group consisting of fluorine, halogenated aliphatic hydrocarbyl and alkyl-silyl-radicals in which at least one halogen atom is linked to a carbon atom or to a silicon atom in position 1 or 2 with respect to the aromatic ring of the Ph* group.

8. Metallocene complex according to claim 1, wherein in formula (III) $R^1$ is bis(fluoroalkyl)benzyl, and each of the remaining $R^2$, $R^3$, $R^4$ and $R^5$ are independently hydrogen or methyl.

9. Metallocene complex according to claim 1, wherein R" in formula (II) is a $C_p$ group containing an $\eta^5$- cyclopentadienyl ring coordinated to the metal M.

10. Metallocene complex according to claim 9, wherein the $C_p$ group is an anion as defined for A.

11. Metallocene complex according to claim 10, selected from the group consisting of:
bis-[$\eta^5$-(4-fluorobenzyl)cyclopentadienyl] zirconiumdichloride;
bis-[$\eta^5$-(4-trifluoromethylbenzyl)cyclopentadienyl] zirconiumdichloride and
bis-[$\eta^5$-(2,4-bistrifluoromethylbenzyl)cyclopentadieny] zrconiumdichloride.

12. Catalyst for the (co)polymerization of ethylene and/or α-olefins comprising at least one metallocene complex according to claim 1, and at least one co-catalyst.

13. Catalyst according to claim 12, wherein the co-catalyst consists of an organo-oxygenated derivative of a metal M' selected from the group consisting of aluminum, gallium and tin.

14. Catalyst according to claim 13, wherein the organo-oxygenated derivative of M' is an aluminoxane.

15. Catalyst according to claim 14, wherein the aluminoxane is methylaluminoxane.

16. Catalyst according to claim 13, wherein the atomic ratio between the metal M, in the metallocene complex, and the metal M', in the co-catalyst, is between 10 and 10000.

17. Catalyst according to claim 16, wherein said atomic ratio is between 200 and 5,000.

18. Catalyst according to claim 12, wherein said cocatalyst is capable of extracting a sigma-bound anionic group therefrom.

19. Catalyst according to claim 12, wherein the cocatalyst is selected from non-protic Lewis acids capable of extracting a sigma-bonded anionic group from a neutral metallocene complex to form a non-co-ordinating anion, and organic salts whose anion is non-coordinating and whose cation is capable of extracting a sigma-bonded anionic group from a neutral metallocene complex to form a neutral compound.

20. Catalyst according to claim 19, wherein the neutral metallocene complex comprises at least one alkyl or amide group linked to the metal M.

21. Catalyst according to claim 12, wherein at least one component selected from the metallocene complex and the co-catalyst is supported on a polymeric, inorganic or organic solid granular carrier.

22. Catalyst according to claim 21, wherein the solid granular carrier is selected from alumina, silica or silicoaluminates.

23. Process for the (co)polymerization of alpha-olefins, comprising feeding at least one alpha-olefin and optional co-monomers to a continuous or batch reactor, and (co) polymerizing the mixture in suspension or solution in a liquid medium, or in the gas phase, in the presence of a polymerization catalyst as defined in claim 12.

24. Process according to claim 23, wherein the alpha-olefin is ethylene.

25. Process according to claim 23, wherein the catalyst is formed in situ in the polymerization reactor by contact of the metallocene complex with said co-catalyst.

26. Process according to claim 25, wherein said co-catalyst is an organo-oxygenated derivative of aluminum.

27. Process according to claim 26, wherein said co-catalyst is an aluminoxane.

* * * * *